United States Patent
Rosa et al.

(10) Patent No.: US 10,433,968 B2
(45) Date of Patent: Oct. 8, 2019

(54) PROSTHESIS FOR JOINT SHOULDER RECONSTRUCTION

(71) Applicant: MEDACTA INTERNATIONAL SA, Castel San Pietro (CH)

(72) Inventors: Andrea Rosa, Azzate (IT); Francesco Siccardi, Castel San Pietro (CH); Massimiliano Bernardoni, Figino (CH)

(73) Assignee: Medacta International SA, Castel San Pietro (CH)

( * ) Notice: Subject to any disclaimer, the term of this patent is extended or adjusted under 35 U.S.C. 154(b) by 23 days.

(21) Appl. No.: 15/559,153

(22) PCT Filed: Mar. 15, 2016

(86) PCT No.: PCT/IB2016/051457
§ 371 (c)(1),
(2) Date: Sep. 18, 2017

(87) PCT Pub. No.: WO2016/147114
PCT Pub. Date: Sep. 22, 2016

(65) Prior Publication Data
US 2018/0064546 A1    Mar. 8, 2018

(30) Foreign Application Priority Data
Mar. 19, 2015   (IT) .............................. MI2015A0414

(51) Int. Cl.
*A61F 2/40*   (2006.01)
*A61F 2/30*   (2006.01)

(52) U.S. Cl.
CPC .............. *A61F 2/4014* (2013.01); *A61F 2/40* (2013.01); *A61F 2002/305* (2013.01);
(Continued)

(58) Field of Classification Search
CPC ............ A61F 2/4014; A61F 2002/4018; A61F 2002/4037; A61F 2002/4051;
(Continued)

(56) References Cited

U.S. PATENT DOCUMENTS 4,225,981 A * 10/1980 Zeibig ................... A61F 2/3609
29/447
2008/0228281 A1   9/2008 Forrer et al.
(Continued)

FOREIGN PATENT DOCUMENTS

EP   2638881 A1   9/2013
FR   2848099 A1 * 6/2004 ............... A61F 2/40
(Continued)

OTHER PUBLICATIONS

International Search Report and Written Opinion dated Jun. 21, 2016, from International Application No. PCT/IB2016/051457, 11 pages.

*Primary Examiner* — David H Willse
*Assistant Examiner* — Javier G Blanco
(74) *Attorney, Agent, or Firm* — Meunier Carlin & Curfman LLC

(57) ABSTRACT

Prosthesis for joint shoulder reconstruction comprising a joint head shaped to provide a spherical type coupling with a concave joint element of a glenoid component. The joint head includes a metallic core and a joint cap made of a plastic material provided with a cavity insertable on an insertion element of the core along a longitudinal direction. The insertion element and the cavity are configured to define shape-coupling means operating by elastic deformation such as to secure the joint cap to the core along the longitudinal direction. A plurality of penetration elements are arranged
(Continued)

Figure 1:
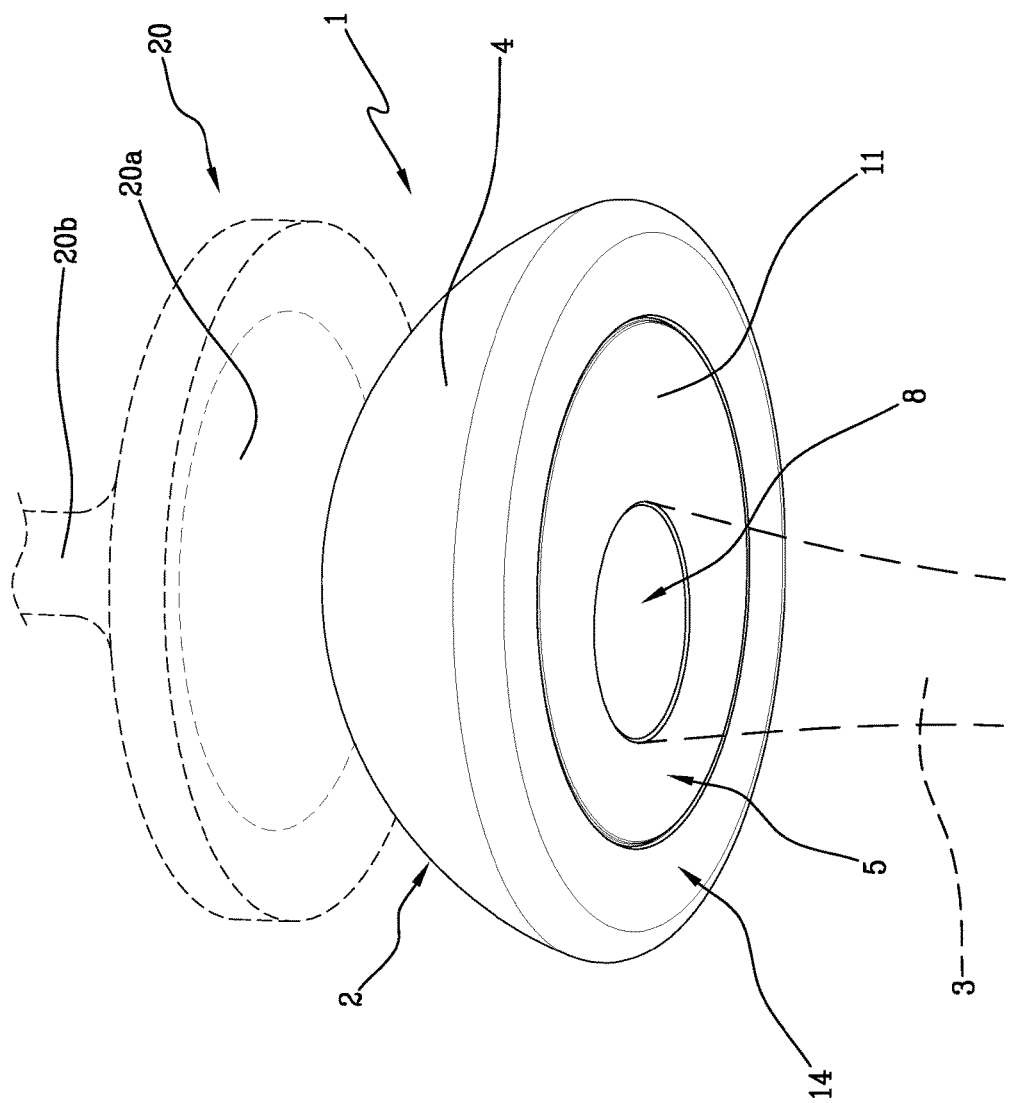

between a plate of the core and a coupling surface of the joint cap to define an anti-rotation mechanism of the joint cap on the core.

13 Claims, 4 Drawing Sheets

(52) U.S. Cl.
CPC ............... *A61F 2002/30331* (2013.01); *A61F 2002/30367* (2013.01); *A61F 2002/30487* (2013.01); *A61F 2002/4018* (2013.01); *A61F 2002/4037* (2013.01)

(58) Field of Classification Search
CPC .. A61F 2002/30331; A61F 2002/30347; A61F 2002/30354; A61F 2002/30367; A61F 2002/30477
See application file for complete search history.

(56) References Cited

U.S. PATENT DOCUMENTS

| 2010/0063593 | A1* | 3/2010 | Klawitter | ............. | A61F 2/4014 623/19.13 |
| 2013/0190882 | A1* | 7/2013 | Humphrey | ............ | A61F 2/4014 623/19.14 |

FOREIGN PATENT DOCUMENTS

| WO | 02/39932 A1 | 5/2002 | | |
| WO | WO 2014067961 A1 * | 5/2014 | ........... | A61F 2/4014 |
| WO | 2015/001525 A1 | 1/2015 | | |

* cited by examiner

PROSTHESIS FOR JOINT SHOULDER RECONSTRUCTION

The present invention relates to a prosthesis for joint shoulder reconstruction.

In particular, the present invention relates to a prosthesis able to allow the anatomical joint shoulder reconstruction.

In general, the prostheses for joint shoulder known today include an element associated with glenoid cavity and a component associated with the humerus, where each of these elements includes a portion for the attachment to the bone and a joint portion.

The joint portions are a ball-shaped portion and the other portion is complementarity shaped with a complementary convexity.

In the case of an anatomical prosthesis, the convex portion is the joint portion of the humerus.

The patent application MI2013A001127 describes the construction of a glenoidal joint portion from a metal material and of the corresponding humerus joint portion from a plastic material.

Currently in the market there are different types of prosthesis for joint shoulder reconstruction, which, however, have some shortcomings.

Firstly, in many applications it is found the phenomenon of the failure and/or breakage of the glenoid component, usually made of polyethylene. This is due to the fact that, because of the conformation of glenoid cavity its self, it is not possible to exceed the thickness of such a portion. This reduced thickness, together with the choice of polyethylene as a construction material, results in a high rate of dissociation from glenoid cavity and a potential increased risk of wear and release of particulate matter.

During normal use of the prosthesis, the glenoid component is subjected to compression and translation loads that stresses the interface with the bone. In the devices completely made of plastic material, this can result in the detachment of the glenoid component.

In this context, the technical task underlying the present invention is to provide a prosthesis for joint shoulder reconstruction that overcomes one or more drawbacks of the prior art mentioned above.

In particular, it is the aim of the present invention provide a prosthesis for joint shoulder reconstruction, which is structurally simple, easy to assemble, and that ensures a more stable tightness in the coupling between the humerus and the glenoid joints.

A further aim of the present invention is to provide a prosthesis for joint shoulder reconstruction that, once assembled, prevent the onset of micromotions between the parts that constitute the prosthesis.

The mentioned technical task and the specified aims are substantially achieved by a prosthesis for joint shoulder reconstruction, including the technical specifications set out in one or more of the appended claims.

In particular, the present invention provides a prosthesis for joint shoulder reconstruction comprising a head element comprising a first bone fixation support and a joint head, and a glenoid component comprising a second bone fixation support and a concave joint element.

The joint head and the concave joint element are shaped so as to provide a spherical type coupling therebetween for the artificial reconstruction of the shoulder joint.

The joint head comprises a metal core comprising a plate from which an insertion element and a joint cape made of plastic material extend, the latter being provided with a cavity insertable on the insertion element of the core along a longitudinal direction.

The plate is provided with means for coupling with the bone fixation support, and the joint cap includes a coupling surface adapted to be arranged at least partly in contact with the plate.

The insertion element and the cavity are configured to define shape-coupling means operating by elastic deformation such as to secure the joint cap to the core along the longitudinal direction.

The prosthesis further comprises a plurality of penetration elements arranged between the plate and the coupling surface around the longitudinal direction to define an anti-rotation mechanism of the joint cap on the core.

Advantageously, the prosthesis as described above allows obtaining a coupling between core and joint cap, ensuring a good tightness of the joint head and preventing any micromovements thereof.

Preferably, the penetration elements are integral to the plate, and configured to penetrate into the joint cap at the coupling surface as a result of the insertion of the joint cap on the core.

Advantageously, the penetration of penetration elements allows a good anchoring between the joint cap and the core, improving its stability.

Preferably, the penetration elements are uniformly distributed around the longitudinal direction, still more preferably over a circular ring around the longitudinal direction.

Preferably, the joint cap has an annular seat around the cavity and the longitudinal direction adapted to receive the plate. Preferably, the coupling surface is defined by a bottom of the seat.

Preferably, the seat has a depth measured along the longitudinal direction that is equal to the height of the plate, whereby, when the joint head is in the assembled configuration, the plate and the joint cap have a planar base surface.

Preferably, the shape-coupling means comprise a lip formed internally of the cavity of the joint cap and extending towards the inside of the same, in a direction transverse to the longitudinal direction, and a cavity of the insertion element adapted to receive the lip.

Preferably, the lip is associated with two grooves arranged on opposite sides along the longitudinal direction configured to allow the elastic deformation of the lip.

Advantageously, the lip improves the stability of the coupling.

Preferably, the insertion element includes a cylindrical portion and a spherical cap-shaped portion.

Preferably, the cavity is complementarity shaped with regard to the insertion element.

Advantageously, the core, once coupled to the joint cap, remains within the volume defined by the joint cap itself.

Preferably, the core is made of cobalt-chrome alloy, and the articular cap is made of plastic material, such as UHMWPE or HIGH CROSS PE.

Figure 2:
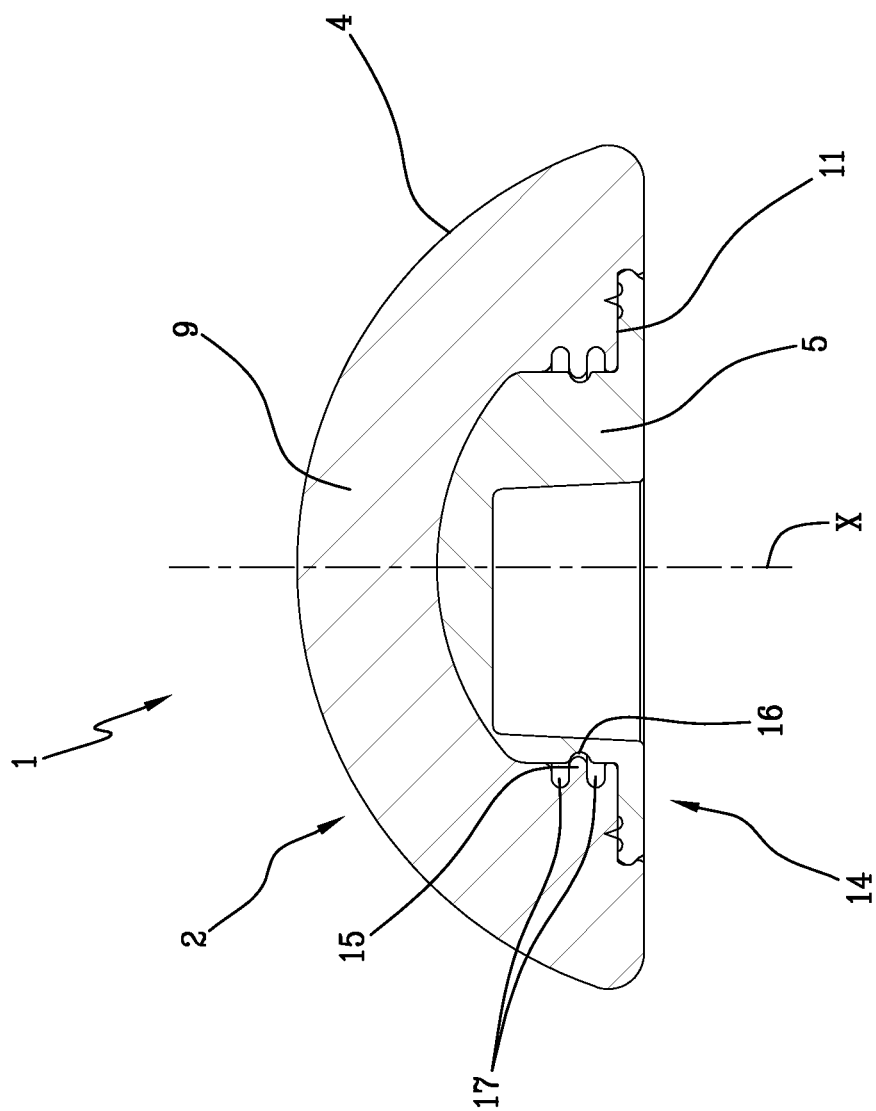
Figure 3:
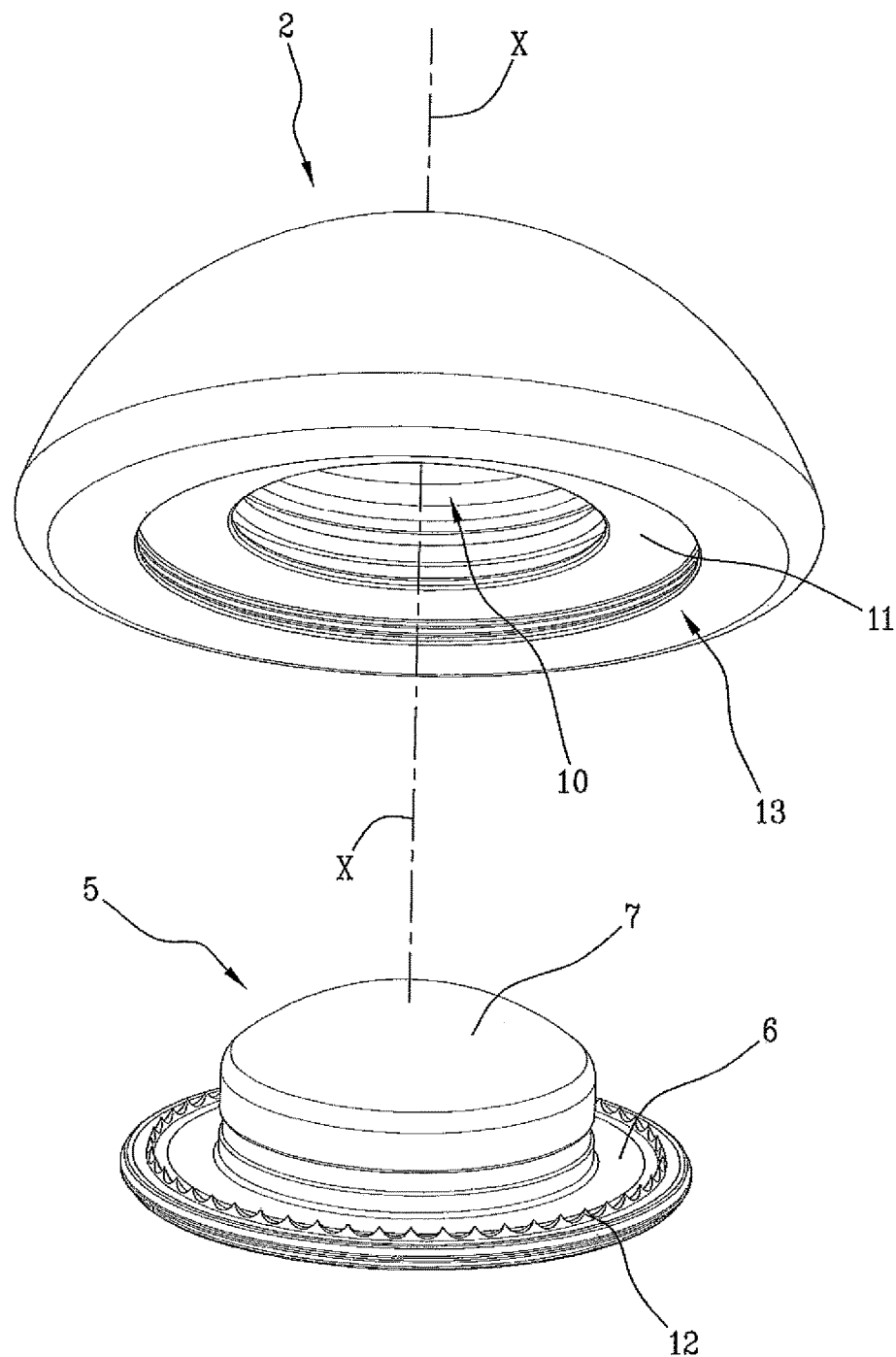
Figure 4:
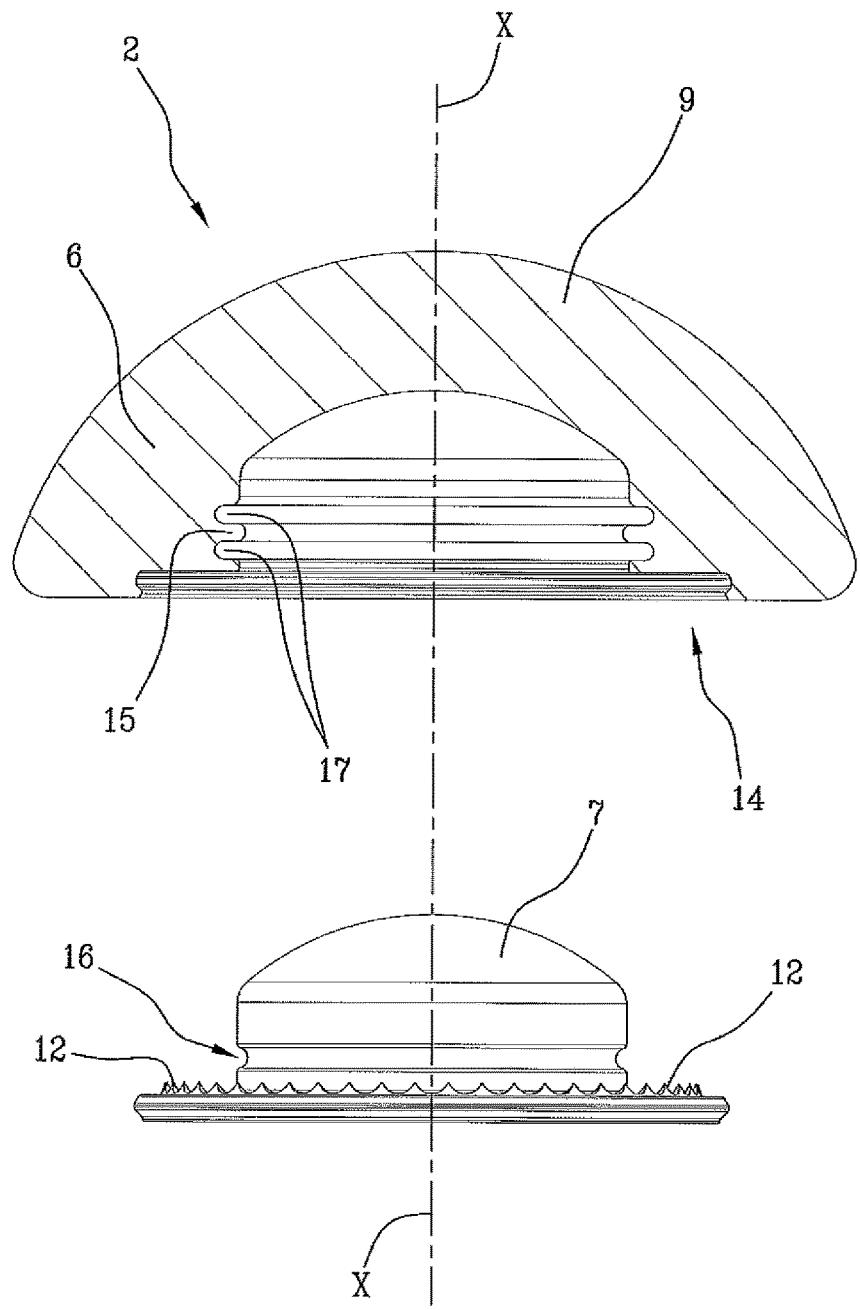

Further characteristics and advantages of the present invention will become more apparent from the description of an exemplary, but not exclusive, and therefore non-limiting preferred embodiment of a prosthesis for joint shoulder reconstruction, as illustrated in the appended figures, in which:

FIG. 1 is a schematic perspective view of a possible embodiment of a head element of the prosthesis for joint shoulder reconstruction in accordance with the present invention, FIG. 2 is a schematic cross section of the head element of FIG. 1, FIG. 3 is an exploded schematic perspective view of the head element of FIG. 1, and FIG. 4 is an exploded schematic cross section of the head element of FIG. 1, With reference to the attached figures, with 1 it has been globally indicated a prosthesis for joint shoulder reconstruction, and hereinafter simply referred to as prosthesis 1.

The prosthesis comprises a head element 1 2 comprising a first bone fixation support 3 and a joint head 4, and a glenoid component 20, comprising a second bone fixation support 20b and a concave joint element 20a.

The joint head 4 and the hollow joint element are shaped so as to provide a spherical type coupling therebetween for the artificial reconstruction of the shoulder joint.

The joint head 4 comprises a metal core 5 comprising a plate 6 from which an insertion element 7 extends.

The plate 6 is provided with means 8 for coupling with the bone fixation support 3.

Preferably, the coupling means 8 are of the Morse taper type, which makes the tightness on the core 5 more stable.

Preferably, the core 5 is made of CoCr alloy (cobalt-chrome).

The joint head 4 then includes a joint cap 9 made of a plastic material provided with a cavity 10 insertable on the insertion element 7 of the core 5 along a longitudinal direction "X".

Preferably, the joint cap 9 is made of UHMWPE or HIGH CROSS PE.

The joint cap 9 comprises a coupling surface 11 suitable to be arranged at least partly in contact with the plate 6.

Advantageously, the insertion element 7 and the cavity 10 are configured to define shape-coupling means operating by elastic deformation such as to secure the joint cap 9 to the core 5 along the longitudinal direction "X".

Preferably, as shown in FIGS. 2 to 4, the insertion element 7 of the core 5 comprises a cylindrical portion and a spherical cap-shaped portion, and the cavity 10 of the joint cap 9 is complementarity shaped with regard to the insertion element 7.

With reference to FIG. 4, preferably, the joint cap 9 has an annular seat 13 around the cavity 10 and the longitudinal direction "X" adapted to receive the plate 6 of the core 5. The coupling surface 11 is defined by a bottom of the seat 13.

Preferably, the longitudinal "X" direction is perpendicular to the plane in which the seat 13 lies.

As shown in the embodiment of this invention shown in FIGS. 3 and 4, preferably the seat 13 has a depth as measured along said longitudinal direction "X" that is equal to the height of the plate 6 whereby, in the assembled configuration of the joint head 2, the plate 6 and the joint cap 9 have a planar base surface 14.

Assembled configuration herein refers to the configuration in which the core 5 is inserted in the joint cap 9.

The prosthesis 1 is preferably assembled during the production phase and supplied as a single device.

The prosthesis 1 of the present invention further comprises a plurality of penetration elements 12 arranged between the plate 6 of the core 5 and the coupling surface 11 of the joint cap 9 around the longitudinal direction "X" to define advantageously an anti-rotation mechanism of the joint cap 9 on the core 5.

Preferably, the penetration elements 22 are integral to the plate 6 and are configured to penetrate into the joint cap 9 at the coupling surface 11 as a result of the insertion of the joint cap 9 on the core 5.

Advantageously, therefore, while in the assembled configuration the joint head 2 is stable, as the penetration elements 12 (also called "spikes"), arranged preferably in the upper part of the plate 6, by penetrating the coupling surface 11, provide a high resistance to the relative rotation, so as to prevent any inadvertent movement between the core 5 and the joint cap 9.

Preferably, the penetration elements 12 are uniformly distributed around the longitudinal direction "X", still more preferably over a circular ring around the longitudinal direction "X".

Preferably, the penetration elements 12 have a sharpened shape that allows advantageously a penetration within the more ductile material of the joint cap 9.

In the embodiment shown in the attached Figures, with particular reference to FIGS. 2 to 4, preferably, the shape-coupling means comprise a lip 15 formed internally of the cavity 10 of the joint cap 9 and extending towards the inside of the same, in a direction transverse to the longitudinal direction "X", and a cavity 16 of the insertion element 7 adapted to receive the lip 15.

Preferably, the lip 15 is associated with two grooves 17 arranged on opposite sides along the longitudinal direction "X" configured to allow the elastic deformation of the lip 15.

Advantageously, the geometry and the size of the cavity 16 and of the lip 15 are in such a way that, while assembling the joint head 4, the lip 15 can be deformed and recover its original geometry within the cavity 16, thus creating a retentive mechanism.

In other words, during the assembly of the core 5 within the joint cap 9 proceeding along the longitudinal direction "X", when the insertion element 7 of the core 5 comes into contact with the lip 15, the latter is deformed and dragged in the longitudinal direction until it comes into contact with the cavity 16 that receives it in a direction transverse, preferably perpendicular, to the longitudinal direction "X".

Advantageously, the coupling between joint cap 5 and core 9 is thus obtained in a simple and practical way, without the need for adhesives or sealants between the parts.

The present invention achieves the proposed objects, overcoming the drawbacks noted in the prior art, and providing to the user a reliable and efficient prosthesis for joint shoulder reconstruction of a patient by providing a coupling between the core 5 and the articular cap 9, which ensures an excellent tightness of the joint head and prevents the corresponding micro-movements.

In addition, the use of a plastic material for the construction of the joint cap 9 allows to realize the joint surface of the glenoid component from a metallic material, preferably a CoCr alloy (chrome-cobalt). The use of a metallic material for the glenoid component, with the same total thickness of the system, makes it possible to use a baseplate as a means of fixing the glenoid cavity, normally used in the case of an inverse prosthesis, which ensures a more stable tightness and significantly reduces the risk of detachment of the prosthesis from the glenoid cavity.

The invention claimed is:

1. A shoulder prosthesis for joint shoulder reconstruction comprising:
    a humeral head component comprising a first bone fixing support and a joint head having a convex articulating surface; and a glenoid component comprising a second bone fixing support and a concave joint element;
said joint head and said concave joint element being shaped so as to provide a spherical type coupling therebetween for the artificial reconstruction of the shoulder joint;
wherein said joint head comprises:
    a metallic core comprising a circular plate from which an insertion element extends, said plate being provided with coupling means with said first bone fixing support,
    a joint cap made in plastic material provided with a cavity insertable on said insertion element of the core along a longitudinal direction, and comprising a coupling surface adapted to be disposed in contact with said plate,
wherein said insertion element and said cavity are configured to define shape-coupling means operating by elastic deformation such as to secure said joint cap to said core along said longitudinal direction, and
in which a plurality of penetration elements are arranged between said plate and said coupling surface around said longitudinal direction to define an anti-rotation mechanism for the joint cap on the core,
wherein said plurality of penetration elements are integral with said plate and distributed along a circular ring around said insertion element.

2. A prosthesis according to claim 1, wherein said penetration elements are integral with said plate and configured to penetrate said joint cap at said coupling surface upon the insertion of the joint cap on the core.

3. A prosthesis according to claim 2, wherein said penetration elements are uniformly distributed around said longitudinal direction.

4. A prosthesis according to claim 3, wherein said penetration elements are uniformly distributed along a circular ring around said longitudinal direction.

5. A prosthesis according to claim 1, wherein said joint cap has an annular seat around said cavity and said longitudinal direction, adapted to receive said plate, and in which said coupling surface is defined by a bottom of said seat.

6. A prosthesis according to claim 5, wherein said seat has a depth as measured along said longitudinal direction that is equal to the height of the plate whereby, in the assembled configuration of the head component, the plate and the joint cap have a planar base surface.

7. A prosthesis according to claim 1, wherein said shape-coupling means comprise a lip formed internally of the cavity of the joint cap and extending towards the inside of the same, in a direction transverse to said the longitudinal direction, and a cavity of said insertion element adapted to receive said lip.

8. A prosthesis according to claim 7, wherein said lip is associated with two grooves arranged on opposite sides along the longitudinal direction configured to allow the elastic deformation of said lip.

9. A prosthesis according to claim 7, wherein said lip is elastically deformable and integrally formed with said joint cap.

10. A prosthesis according to claim 1, wherein said insertion element comprises a cylindrical portion and a spherical cap-shaped portion, said cavity being counter-shaped with respect to said insertion element.

11. A prosthesis according to claim 1, wherein said core is made of CoCr alloy and said joint cap is made of UHMWPE or HIGH CROSS PE.

12. A prosthesis according to claim 1, wherein the coupling means comprises an opening crossing said plate.

13. A prosthesis according to claim 1, wherein the coupling means of said plate are of the morse taper type.

\* \* \* \* \*